US00PP35830P2

(12) United States Plant Patent
Bedford et al.

(10) Patent No.: US PP35,830 P2
(45) Date of Patent: May 28, 2024

(54) APPLE TREE NAMED 'MN33'

(50) Latin Name: *Malus domestica*
Varietal Denomination: MN33

(71) Applicant: Regents of the University of Minnesota, Minneapolis, MN (US)

(72) Inventors: David S. Bedford, New Germany, MN (US); James J. Luby, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/218,062

(22) Filed: Jul. 4, 2023

Related U.S. Application Data

(60) Provisional application No. 63/390,334, filed on Jul. 19, 2022.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Penny J Aguirre

(57) ABSTRACT

A new cultivar of apple tree 'MN33' that is characterized by its fruit with a texture that is very crisp and juicy, its fruit with a flavor that is sweet/tart, well balanced, and slightly reminiscent of tropical fruits, its fruit with a storage life of 132 to 154 days without using CA or 1-MCP, its fruit skin that is 85% to 95% red in color, its fruit that is medium to large in size, and its moderate resistance to apple scab.

3 Drawing Sheets

Botanical classification: *Malus domestica.*
Varietal denomination: 'MN33'.

BACKGROUND OF THE INVENTION

The present invention relates to a new and distinct cultivar of apple tree, botanically known as *Malus domestica* 'MN33', referred to hereafter by its cultivar name, 'MN33'.

'MN33' arose from an ongoing breeding program at a research center in Excelsior, Minnesota. The goal of the breeding program was to select a new cultivar of apple tree with sufficient cold hardiness to grow and fruit at commercial levels in USDA Hardiness Zone 4 with fruit that has good flavor, texture, and an attractive appearance.

The new apple tree arose from a cross made in 2001 between 'Honeycrisp' (U.S. Plant Pat. No. 7,197) as the female parent and 'Minnewashta' (U.S. Plant Pat. No. 11,367) as the male parent. 'MN33' was selected as a single unique seedling tree by the Inventors from amongst the seedling from the above cross.

Asexual propagation of the new cultivar was first accomplished by bud grafting in 2008 under the direction of the Inventors in Excelsior, Minnesota. Asexual propagation by bud grafting and bench grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'MN33' as a unique cultivar of apple tree.

1. 'MN33' exhibits fruit with a texture that is very crisp and juicy.
2. 'MN33' exhibits fruit with a flavor that is sweet/tart, well balanced, and slightly reminiscent of tropical fruits.
3. 'MN33' exhibits fruit with a storage life of 132 to 154 days without using CA (controlled atmosphere) or 1-MCP (1-methylcyclopropene).
4. 'MN33' exhibits fruit skin that is 85% to 95% red in color.
5. 'MN33' exhibits fruit that is medium to large in size (2.9-3.2"/73-82 mm).
6. 'MN33' exhibits moderate resistance to apple scab.
7. 'MN33' exhibits a mid to late fruit harvest season in Carver County, Minnesota.

The female parent of 'MN33', 'Honeycrisp', differs from 'MN33' in having fruit with less coverage of red overcover, fruit that ripens slightly earlier (4 to 7 days), and a less vigorous growth habit. The male parent of 'MN33', 'Minnewashta', differs from 'MN33' in having fruit with less coverage of red overcover, fruit that ripens earlier (14 to 20 days), and in being less resistant to apple scab. 'MN33' can be most closely compared to *Malus domestica* cultivars, 'Minneiska' (U.S. Plant Pat. No. 18,812) and 'MN55' (U.S. Plant Pat. No. 26,412). 'Minneiska' is similar to 'MN33' in being a sibling seedling of the same cross and in having similar fruit texture. 'MN55' is similar to 'MN33' in having 'Honeycrisp' as the female parent and in having similar fruit texture. Both 'Minneiska' and 'MN55' differ from 'MN33' in having fruit that ripens earlier.

BRIEF DESCRIPTION OF THE DRAWINGS

The accompanying color photographs were taken of fruit harvested from 'MN33' trees that were grown in a trial plot for approximately 12 years in Excelsior, Minnesota.

The photograph in FIG. 1 provides a view of the stem end of fruit of 'MN33'.

Figure 1:
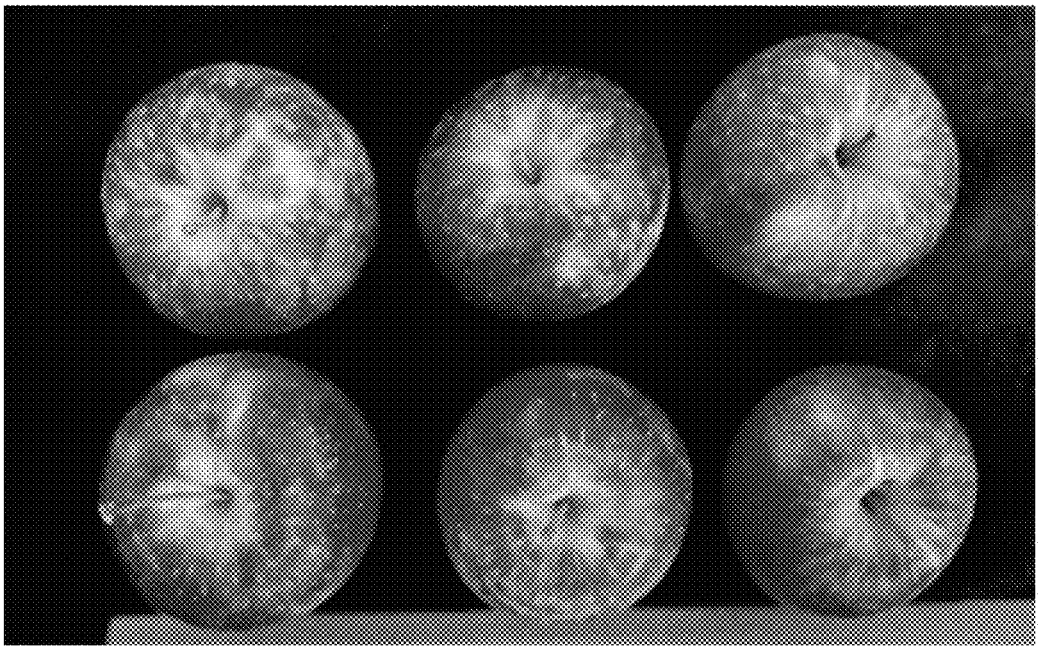
Figure 2:
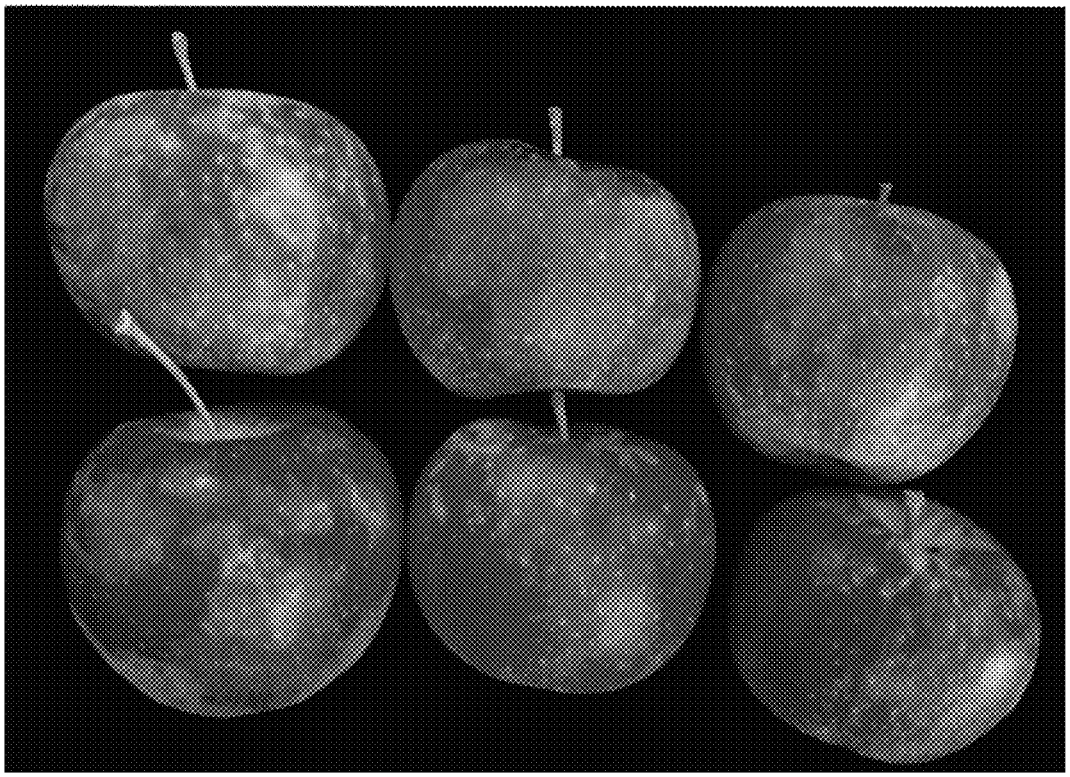

The photograph in FIG. 2 provides a side view of the fruit of 'MN33'.

Figure 3:
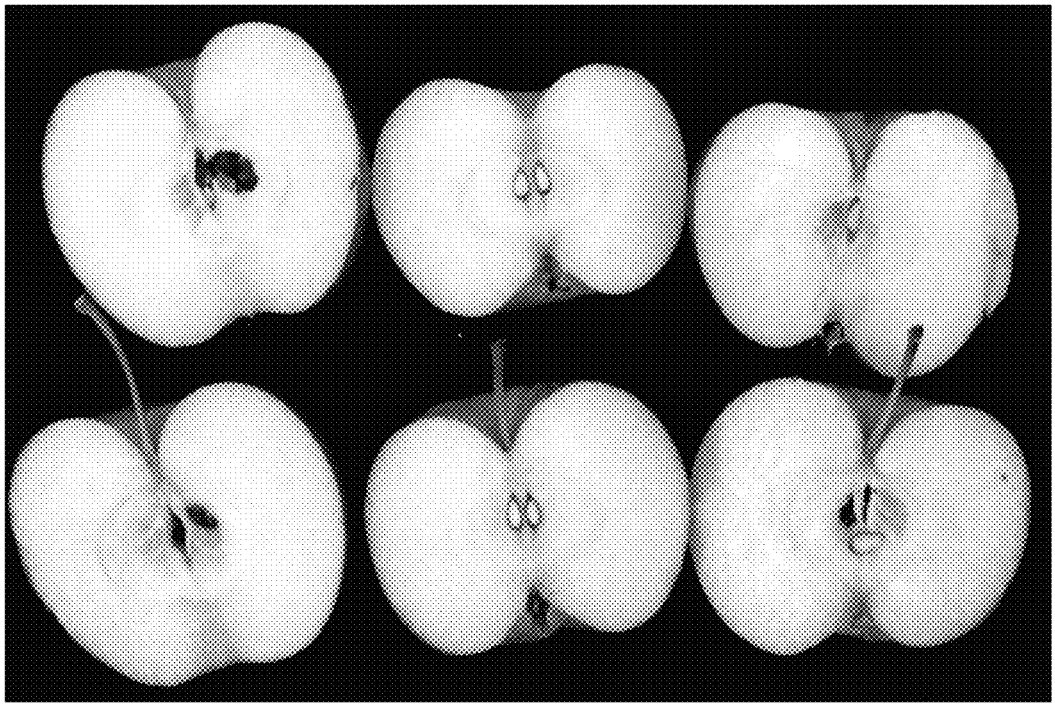

The photograph in FIG. 3 provides a view of fruit cut longitudinally of 'MN33'.

Figure 4:
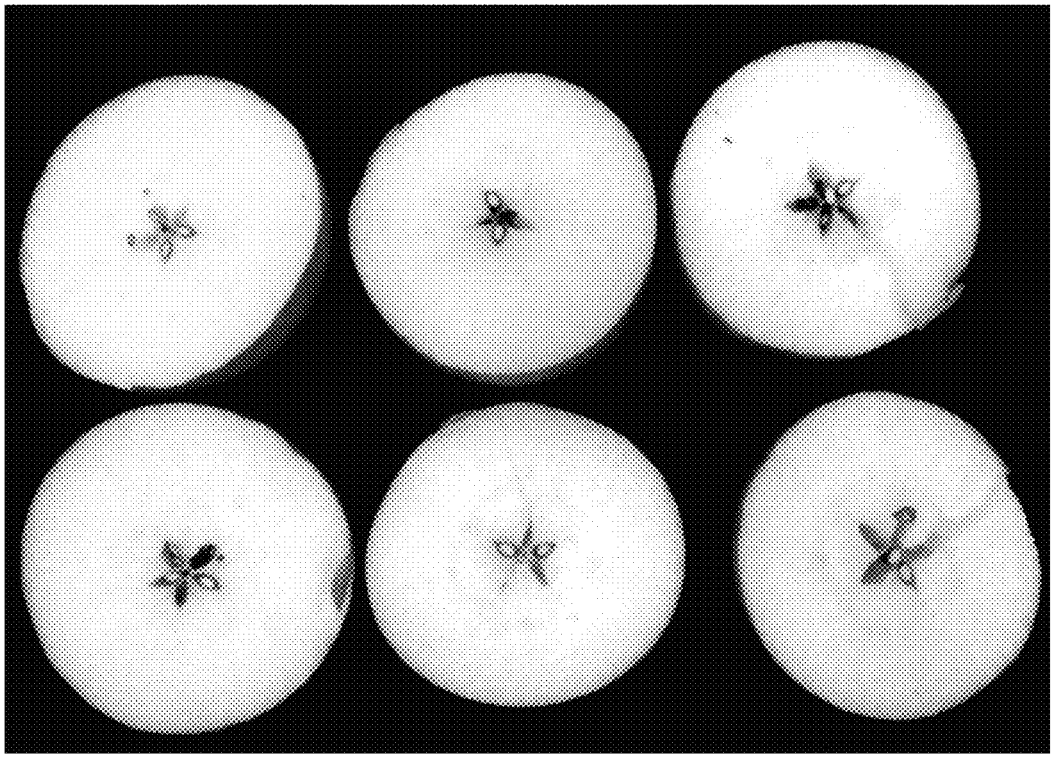

The photograph in FIG. 4 provides a view of fruit cut horizontally of 'MN33'.

Figure 5:
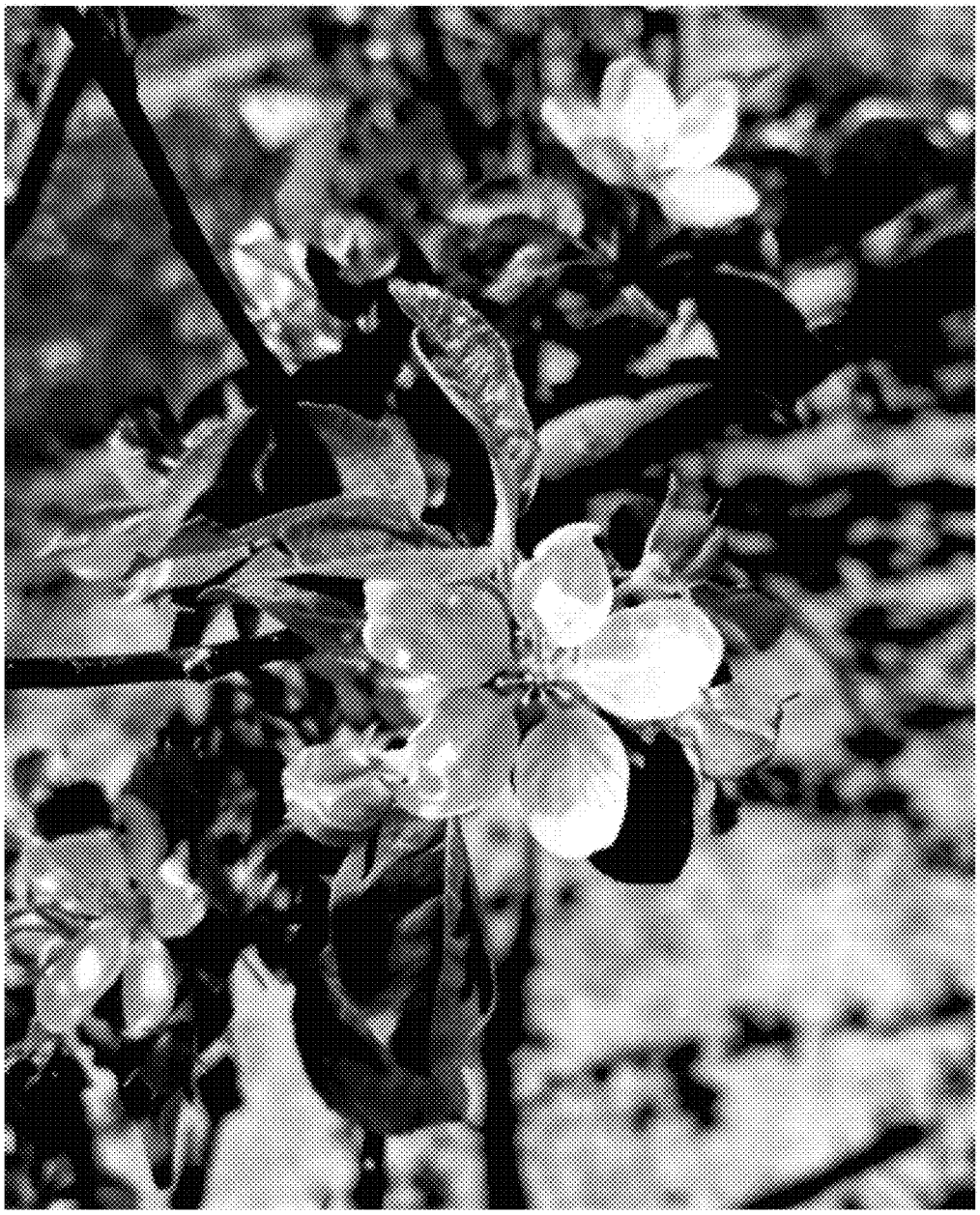

The photograph in FIG. 5 provides a close-up view of a flower and flower buds of 'MN33'.

The colors in the photograph are as close as possible with the photographic and printing technology utilized and the color values cited in the detailed botanical description accurately describe the colors of the new apple tree.

DETAILED BOTANICAL DESCRIPTION

The following is a detailed description of the new apple variety as observed on trees grown for 12 years in Excelsior, Minnesota. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

Tree description:

*Habit*.—Upright to spreading.

*Growth rate*.—Moderately vigorous.

*Diseases and pests*.—Moderate resistance to apple scab has been observed (caused by *Venturia inaequalis*), no resistance or susceptibility to pests has been observed.

*Cold hardiness*.—At least in U.S.D.A. Zone 4.

*Tree size*.—A tree twelve years in age will reach 3.4 to 3.7 m in height and 2.1 to 2.4 m in spread on Malling 26 rootstock.

Branch description:

*Branch shape*.—Rounded, strong.

*Branch color*.—Young; 167A, mature; 183A and N200A, trunk; N200A, N200B and N200C.

*Branch size*.—Main branches; an average 2.4 m in length, 10 cm in diameter, lateral branches; an average of 1.5 m in length and 4 cm in diameter, tertiary branches; an average of 68 cm in length and 3 cm in diameter, trunk; 10.2 to 12.7 cm in diameter at 30.5 cm above the soil level.

*Stem surface*.—Young stems; glabrous and slightly glossy, mature stems; matte, trunk; exfoliating, rugose and matte, all branches moderately covered with lenticels; an average of 1 mm in length and 1.2 mm in width, oval to linear in shape, 156C in color.

*Branching*.—Spreading, 1 main branch (trunk), average of 27 lateral branches, 14 tertiary branches per lateral branch.

*Branch strength*.—Intermediate.

*Branching habit*.—Spreading.

*Branch internode length*.—Average of 3 cm.

*Stipules*.—2 per petiole, leafy and drop when the leaf matures, linear in shape, acute apex, cuneate base, average of 1.5 cm in length and 1 mm in width, 139B in color, glabrous surface, margins moderately covered with soft pubescent hairs; an average of 0.5 mm in length, NN155C in color.

*Angle of bearing branches*.—Typically 60° to 85°.

*Predominance of bearing*.—Both spurs and shoots.

*Branch frequency*.—Medium.

Leaf description:

*Leaf orientation*.—Upright and outward.

*Leaf arrangement*.—Whorled.

*Leaf division*.—Simple.

*Leaf shape*.—Ovate.

*Leaf quantity*.—An average of 13 per spur.

*Leaf size*.—Average of 5.5 cm in length, 3.5 cm in width.

*Leaf apex*.—Acuminate.

*Leaf base*.—Acute.

*Leaf surface*.—Young leaves; upper surface glossy, young leaves lower surface matte and densely covered with soft woolly pubescence, 149D in color, up to 1 mm in length, mature leaves upper surface; matte, mature leaves lower surface; slightly glossy, sparsely covered with soft woolly pubescence; 149D in color, up to 1 mm in length.

*Leaf margin*.—Serrate.

*Leaf color*.—Young and mature upper surface; 146A, young and mature lower surface; 147D.

*Leaf venation*.—Pinnate, color of both surfaces; 145D.

*Petiole*.—Mostly rounded in shape, average of 3 cm in length and 2 mm in diameter, upper and lower surface are densely covered with soft woolly pubescence, 149D in color, up to 1 mm in length, slightly glossy, young petioles flushed with 180A.

Flower description:

*Beginning flowering date*.—Ranging from April 23rd (early blooming years) to May 24th (late blooming years) and extending 4 to 8 days depending on weather conditions in Excelsior, Minnesota.

*Number of flowers*.—5 to 6 per spur.

*Inflorescence type*.—Corymb of rotate flowers.

*Flower buds*.—At pink tip stage; ranging between 60A to 60B and 62A in color, round to conical in shape, average of 1.4 cm in length and 1 cm in diameter.

*Flower size*.—Average of 5 cm in diameter and 1 cm in depth.

*Flower fragrance*.—Moderate and typical floral apple blossom.

*Flower aspect*.—Upright, outward and rotate.

*Petals*.—5 per flower, un-fused, sometimes overlapping, ovate in shape, obtuse apex, entire and slightly undulate margins, average of 1.5 cm in width and 2.3 cm in length, color: when opening upper surface; NN155A, flushed with 68A around the margins and the veins, when opening lower surface; NN155A, flushed with 68A and 68B at the margins, veins and center, top flushed with 1D, when fully open upper surface; NN155A, sometimes veins are flushed with 63B, when fully open lower surface; NN155A, mottled with 63B, fully mature upper and lower surface; NN155A.

*Sepals*.—5, triangular in shape, entire margin, acute apex, fused base, curved downward, average of 1 cm in length and 3 mm in width, both surfaces are densely covered with soft woolly pubescence, 149D in color, up to 1 mm in length, surface color where sections of the pubescence are not as dense; 141A in color, tips 187A.

*Pedicel.*—182A in color, average of 2 cm in length and 3 mm in width, surface is densely covered with soft woolly pubescence, 149D in color, up to 1 mm in length.

Reproductive organs:

*Pistil.*—5, 6 mm in length, 0.8 mm in diameter, style; 5.5 mm in length, 0.8 mm in diameter, 145A in color, surface is slightly glossy and densely covered with fine minute puberulent hairs matching surface color, stigma; round in shape, 0.5 mm in diameter, 13B in color, ovary is pubescent and 139D in color.

*Stamens.*—Average of 18, anther; club-shaped, dorsifixed, 1 mm in diameter, 10B in color, pollen; moderate in quantity, 10A to 10D in color.

Fruit description:

*Fruit size.*—Medium-large, average of 7.5 cm in width and 6.2 cm in height.

*Position of maximum diameter.*—Slightly above the midway point between proximal and distal ends.

*Fruit shape.*—Globose-flat globose.

*Fruit symmetry.*—Asymmetrical.

*Fruit prominence of ribbing.*—Absent.

*Size of eye (calyx).*—6 mm in diameter.

*Persistence of calyx.*—Present.

*Length of sepal.*—4.5 mm.

*Spacing of sepals at base.*—Touching, non-overlapping.

*Depth of eye basin.*—6 mm.

*Width of eye basin.*—Average of 3.1 cm.

*Thickness of stalk.*—Medium.

*Stalk size.*—Average of 2 mm in width and 2.2 cm in length.

*Depth of stalk cavity.*—Average of 1.2 cm.

*Width of stalk cavity.*—Average of 1.8 cm.

*Relief of surface.*—Slightly hammered.

*Bloom of skin.*—Moderate to heavy.

*Waxiness of skin.*—Moderate.

*Thickness of skin.*—Medium.

*Skin color.*—85 to 90% covered with a blend of 46A, N34 and 59A over a background color of 13D.

*Presence of russet.*—Low, positioned around the stalk cavity.

*Lenticels.*—Medium (average of 1 mm in diameter), moderately prominent.

*Color of flesh.*—NN155A.

*Distinctness of core line.*—Weak.

*Aperture of locules.*—Moderately open.

*Fruit set.*—Intermediate to good.

*Fruit maturity date.*—Medium, typically September 23rd to October 3rd in central Minnesota.

*Seed.*—A blend of N199B and 199C in color, deltoid in shape, an average of 7 mm in length and 5 mm in diameter.

*Browning of flesh.*—Weak.

*Firmness (without skin).*—15.3 to 18.6 pounds of pressureat harvest with the skin removed as measured by a Magness penetrometer.

*Texture of flesh.*—Crisp.

*Cropping frequency.*—Annual.

*Fruit flavor.*—Well balanced with moderate fruity flavor and slightly tropical.

*Fruit weight.*—Ranges from 160 to 175 g.

*Fruit productivity.*—Moderate.

*Juiciness.*—Juicy.

*Acidity.*—Moderate.

*Brix.*—Average of 15.9°.

*Storage life.*—132 to 154 days in ambient atmosphere storage (average temperature of 34° F.).

*Market use.*—Fresh Fruit.

It is claimed:

1. A new and distinct variety of apple tree named 'MN33' as herein illustrated and described.

* * * * *